US010526265B2

(12) United States Patent
Rohlfsen

(10) Patent No.: US 10,526,265 B2
(45) Date of Patent: *Jan. 7, 2020

(54) METHOD FOR CULTIVATION OF MONARDA FISTULOSA FOR PRODUCTION OF THYMOQUINONE

(71) Applicant: PRAIRIE PHARMS, LLC, Nora Springs, IA (US)

(72) Inventor: William Rohlfsen, Mason City, IA (US)

(73) Assignee: Prairie Pharms, LLC, Nora Springs, IA (US)

(*) Notice: Subject to any disclaimer, the term of this patent is extended or adjusted under 35 U.S.C. 154(b) by 89 days.

This patent is subject to a terminal disclaimer.

(21) Appl. No.: 15/719,211

(22) Filed: Sep. 28, 2017

(65) Prior Publication Data

US 2018/0079703 A1    Mar. 22, 2018

Related U.S. Application Data

(63) Continuation of application No. 14/286,543, filed on May 23, 2014, now Pat. No. 9,776,939, which is a continuation-in-part of application No. 13/804,026, filed on Mar. 14, 2013, now Pat. No. 9,073,824, and a continuation-in-part of application No. 13/359,045, filed on Jan. 26, 2012, now Pat. No. 9,029,610.

(51) Int. Cl.

| C07C 37/68 | (2006.01) |
| C07C 37/76 | (2006.01) |
| C07C 29/80 | (2006.01) |
| A01D 45/00 | (2018.01) |
| C07C 37/00 | (2006.01) |
| C07C 46/10 | (2006.01) |
| A01G 22/00 | (2018.01) |
| A01D 91/04 | (2006.01) |

(52) U.S. Cl.
CPC ............ *C07C 37/004* (2013.01); *A01D 45/00* (2013.01); *A01D 91/04* (2013.01); *A01G 22/00* (2018.02); *C07C 29/80* (2013.01); *C07C 37/68* (2013.01); *C07C 37/76* (2013.01); *C07C 46/10* (2013.01); *C07C 2601/16* (2017.05)

(58) Field of Classification Search
CPC ....... C07C 37/004; C07C 29/80; C07C 37/68; C07C 34/76; A01D 45/00
See application file for complete search history.

(56) References Cited

U.S. PATENT DOCUMENTS

| 5,591,435 | A | 1/1997 | Vaccarello-Dunkel et al. |
| 6,632,798 | B2 | 10/2003 | Hamdi et al. |
| 6,649,650 | B2 | 11/2003 | Rao et al. |
| 6,649,660 | B2 | 11/2003 | Ninkov |
| 6,902,726 | B1 * | 6/2005 | Varel ............... A61L 2/18 424/76.6 |
| 8,557,306 | B2 | 10/2013 | Tripp et al. |
| 9,029,610 | B2 * | 5/2015 | Rohlfsen ............... A01G 22/00 568/756 |
| 9,040,103 | B2 | 5/2015 | Marrot et al. |
| 9,073,824 | B2 * | 7/2015 | Rohlfsen ............... A01G 22/00 |
| 9,745,242 | B1 | 8/2017 | Greaves et al. |
| 9,776,939 | B2 * | 10/2017 | Rohlfsen ............... A01G 22/00 |
| 10,138,194 | B2 | 11/2018 | Greaves et al. |
| 2003/0017334 | A1 | 1/2003 | Griffith et al. |
| 2003/0118677 | A1 | 6/2003 | Donato et al. |
| 2004/0009239 | A1 | 1/2004 | Shyur et al. |
| 2006/0194698 | A1 | 8/2006 | Gwinn et al. |
| 2010/0323041 | A1 | 12/2010 | Cyr |
| 2013/0316432 | A1 | 11/2013 | Cyr |
| 2014/0255370 | A1 | 9/2014 | Schreuder et al. |
| 2016/0213727 | A1 | 7/2016 | Rohlfsen |

FOREIGN PATENT DOCUMENTS

WO    03068158 A2    8/2003

OTHER PUBLICATIONS

Mazza et al. Flavour and Fragrance Journal 1987, 2, 129-132 (Year: 1987).*
Ivankovic et al. Exp. Oncol. 2006, 28, 3, 220-224 (Year: 2006).*
Gunes et al. Ind. Eng. Chem. Res. 2006, 45, 54-61 (Year: 2006).*
Journal of the Chemical Society, Abstracts of Papers, 1901, vol. LXXX, p. 598 (Year: 1901).*
CAS Registry Entry for Registry No. 2217-60-9, which entered STN on Nov. 16, 1984 (Year: 1984).*
Seymour et al. "Six Basic Elements for a Successful Native Grass and Forb Establishment," 2008, obtained from https://www.tn.gov/twra/pdfs/nativegrass6elements.pdf (Year: 2008).*
Carnat et al. Flavour and Fragrance Journal 1991, 6, 79-80 (Year: 1991).*
Bakkali, F., et al. "Biological Effects of Essential Oils—A Review", Food and Chemical Toxicology, Science Direct, 46 (2008) pp. 446-475.
Lange, B. Markus, et al. "Genetic Engineering of Essential Oil Production in Mint", Plant Biology (1999) 2, pp. 139-144.

(Continued)

*Primary Examiner* — Matthew P Coughlin
(74) *Attorney, Agent, or Firm* — McKee, Voorhees & Sease, PLC

(57) ABSTRACT

A method for cultivating *Monarda fistulosa* for production of thymoquinone includes planting seeds at rates between about 2.5 and about 5 pounds per acre, preferably about 4 pounds per acre. The heavy rate of planting produces plants bearing oil without weed contamination and reduces herbicide use due to production of natural herbicides by the *monarda* plants. Seeding and mowing the first season, and harvesting in seasons thereafter reduce costs. The method results in increased production of essential oils including thymoquinone and thymohydroquinone at levels up to about 40% or more of recovered oils, and which may be distilled from the plant.

9 Claims, 5 Drawing Sheets

(56) References Cited

OTHER PUBLICATIONS

Seymour, et al. "Six Basic Elements for a Successful Native Grass and Forb Establishment", 2008, obtained from https://www.tn.gov/twra/pdfs/nativegrass6elements.pdf.

Weaver, David K., et al. "Dried Leaves from Rocky Mountain Plants Decrease Infestation by Stored-Product Beetles", Journal of Chemical Ecology, (1995) vol. 21, No. 2, pp. 127-142.

Mazza, G., et al. "Essential Oil of Monarda Fistulosa L. Var. Menthaefolia, a Potential Source of Geraniol", Flavour and Fragrance Journal (1987) vol. 2, pp. 129-132.

Daba, Mohamed Hesham, et al. "Hepatoprotective Activity of Thymoquinone in Isolated Rat Hepatocytes", Toxicology Letters, (1995) 95: pp. 23-29.

Janke, et al. "A Grower's Guide, Beebalm/Monarda", Kansas State University Agricultural Experiment Station and Cooperative Extension Service, MF-2605, May 2004.

Pandey, et al. "Medicinal Plants Derived Nutraceuticals: A Re-Emerging Health Aid", International Journal of Pharma and Bio Sciences (2011), vol. 2, Issue 4, pp. 419-441.

Plants Database, Wild Bergamot (*Monarda fistulosa* var. fisUosa) in in the Bee Balms Database, Garden.org, recovered from https://garden.org/plants/view/226613/wild-bergamot-monarda-fistulosa-var-fistulosa/ on Feb. 27, 2017.

North Carolina Wildflower Program, Monarda didyma, obtained from https://web.archive.org/web/20100602004505/ http://www.ncdot.gov/doh/operations/dp_chief_eng/roadside/wildflowerbook/wildflower/18b.html, archived on Jun. 2, 2010.

Taborsky, et al. "Identification of Potential Sources of Thymoquinone and Related Compounds in Asteraceae, Cupressaceae, Lamiaceae, and Ranunculaceae Families" Central European Journal of Chemistry, (2012) 10, pp. 1899-1906.

Mazza, G., et al. "Monarda: A Source of Geraniol, Linalool, Thymol and Carvacrol-rich Essential Oils" (1993), pp. 628-631, In:J. Janick and J.E. Simon (eds), New Crops, Wiley, New York.

Keefover-Ring, K., "Monarda Fistulosa: Making Good Scents in Colorado", Aquilegia, Newsletter of the Colorado Native Plant Society (2006) vol. 30, No. 2, pp. 3-4.

Keefover-Ring, K., One Chemistry—Two Continents: Function and Maintenance of Chemical Polymorphism in the Mint Family (Lamiaceae), University of Colorado Thesis (2008).

Rohlfsen, U.S. Appl. No. 15/006,611, filed Jan. 26, 2016.

Herbalpedia, Entry for Bergamot, obtained from http://www.herbalpedia.com/BERGAMOT.pdf on Jun. 26, 2017.

\* cited by examiner

Compound (%)

| Sample # COMPOUND (%) | 1 | 2 | 3 | 4 | 5 | 6 | 7 | 8 | 9 | 10 | 11 | 12 |
|---|---|---|---|---|---|---|---|---|---|---|---|---|
| Thymoquinone | 42.77 | 41.4 | 40.7 | | 39.1 | 38.4 | 37.0 | 36.3 | 35.0 | 34.7 | 33.9 | 33.8 |
| Carvacrol | 8.2 | 4.5 | 2.8 | | 3.0 | 24.6 | 23.0 | 25.4 | 20.2 | 24.4 | 26.5 | 27.4 |
| Thymol | 6.5 | 45.8 | 10.3 | | 39.0 | 0.3 | 0.0 | 0.0 | 0.5 | 0.0 | 0.0 | 1.0 |

FIG. 5

METHOD FOR CULTIVATION OF MONARDA FISTULOSA FOR PRODUCTION OF THYMOQUINONE

CROSS-REFERENCE TO RELATED APPLICATIONS

This is a continuation application of U.S. Ser. No. 14/286,543, filed May 23, 2014, which is a continuation-in-part of U.S. Ser. No. 13/804,026 filed Mar. 14, 2013 (now U.S. Pat. No. 9,073,824, issued Jul. 7, 2015), and U.S. Ser. No. 13/359,045 filed Jan. 26, 2012 (now U.S. Pat. No. 9,029,610, issued May 12, 2015.

FIELD OF THE INVENTION

The present invention relates to a method for producing *Monarda Fistulosa* for the efficient harvest of thymoquinone essential oil.

BACKGROUND OF THE INVENTION

Some plant essential oils have long been known to possess properties that can be employed as food or flavoring, and for medicinal and industrial purposes. Different plant species provide different oils. For example, peppermint for the peppermint plant's leaves which provides flavoring is sometimes used as an aid for digestive issues. And clove oil is extracted from flowers and used for flavoring, scent, and various historical medicinal purposes. *Eucalyptus* oil, produced from the leaves of *Eucalyptus globulus* is used in many cleaning solutions and as an antiseptic.

As another example, *Monarda fistulosa* and many other plants belonging to the true mint family i.e. labiate, have been a source of geraniol, thymol and carvacrol essential oils. Geraniol is used in perfumes. Thymol is used in mouthwash as an antiseptic and has been shown to have antifungal activity, as well. It is known that Carvacrol may also be used as an antimicrobial, antifungal and as a flavoring. Thymoquinone and Thymohydroquinone are also essential oils present in the *Monarda fistulosa* plant. Thymoquinone has recently been discovered to have specific effects on some mammalian cancers and is a phytochemical found in the plant *Nigella sativa* and several other plants. It is an antioxidant and has been shown to effect or decrease damage caused by heart, liver and kidney diseases in animal studies. Thymoquinone is an angiogenesis inhibitor and appears to have analgesic and anti-convulsant effect. Tests have shown thyrnoquinone kills pancreatic cancer cells and may have promise related to controlling certain kinds of epileptic seizures.

Although it would seem likely that every plant of a species would have a similar oil content profile, it has been found instead that different races of a plant species may provide different ratios of the essential oils they produce. There are many theories as to the reasons for these differences which include response to climate, moisture levels, nutrient levels, evolution due to these pressures, etc.

Many plants are indigenous to a particular geographic area and/or climate. Historically, those who sought plant oils would gather many plants from their natural habitat. Some plants containing desirable oil have been cultivated for research purposes related to the oil. However, commercial use of *Monarda* to date includes propagation for seeds to add color to natural prairie and wildflower seed mixes, or selected Sweet *Monarda* may be grown to produce geraniol used in perfumes.

Cultivation for research or seed purposes may include transfer of the plants from their native growth area to a different geography, climate or soil type or a combination of these. Natural travel of seeds from one area to another may also result in new habitats for a given plant wherein the new habitat may include differing climate, soil, or pests from those in the original habitat. It has been noted that such transfer may result not only in different physical characteristics of the plant in response to the environmental differences, but that these changes may, in turn, result in different ratios of the oils produced by the plant.

*Monarda* is a genus consisting of at least about 16 species. The plants are erect, herbaceous, annual or perennial, in the family Lamiaceae and are native to North America. The plants typically range in height from 1 to 3 feet (0.2 to 0.9 m), the plants have an equal spread, with slender and long-tapering (lanceolate) leaves. The leaves, when crushed, exude a spicy, highly fragrant oil. Common names include bee balm, horsemint, and bergamot, among others. When the term "*Monarda*" is used herein it is understood that it includes plants known by these names, as well, provided the plant meets the characteristics of the *Monarda* genus.

In the case of *Monarda fistulosa*, several studies provide information pertinent to the present invention. In the early 1970's anew chemical race of *Monarda fistulosa* was discovered in Manitoba Canada and studied. (MARSHALL H, H, and R. W. SCORA.1972. A new chemical race of *Monarda fistulosa* (Labiatae). Can. J. Bot. 50: 1845-1849.) *Monarda fistulosa* is widely distributed throughout North America and a plant had been discovered having a different scent than most others. It was dubbed "sweet *Monarda*" due to the scent which was the only difference discernable without chemical testing. Other Sweet *Monarda* plants were then found, albeit far more scarce than the dominant type. The Sweet *Monarda* plants were generally more scarce and did not grow at many of the study's collection sites. Typically, the sweet *Monarda* plants were collected on light sand and stabilized dunes.

Sweet *Monarda* was crossed with other *Monarda*. Then the oils of the crosses and of the Sweet *Monarda* were studied using chromatography of the leaf oil. The researchers found that oil from the nonsweet *Monarda* was moderately viscous and was reported clear and colorless whereas oil from Sweet *Monarda* smelled sweet. Chromatograms showed that oil from the Sweet *Monarda* included far more geraniol but far less thymol and carvacrol than the nonsweet *Monarda* plants tested.

Another study completed in 1993 looked at *Monarda* as a source of certain oils, specifically, geraniol, linalool, thymol and carvacrol. This study also presented the idea that plants of a given species but grown and maintained in different geographical regions may yield different oils. (Mazza, G., F. A. Kiehn, and H. H. Marshall. 1993. *Monarda*: A source of geraniol, linalool, thymol and carvacrol-rich essential oils. p. 628-631. In: J. Janick and J. E. Simon (eds.), New crops. Wiley, New York.)

When *Monarda fistulosa* is crossed with *M. didyma* a vigorous hybrid is produced that yields geraniol, linalool, thymol, carvacrol and other terpenes. However, multiple crosses as conducted by the study resulted in a sterile plant which had to be propagated by division. The study employed a planting rate of 10,000 plants/ha (or 24,000/acre). The study acknowledged that propagation via crown divisions would be easily achieved but, because crown division is cumbersome and inefficient, the study recommended using stem cuttings instead. The cuttings were recommended to be 10-12 cm in length with their bases dipped in rooting compound and then placed in sand in a misting chamber. Roots were reportedly produced in a week using this method and recommended to be transplanted in 14-16 days. Further, weeds were reported as being easily controlled by herbicides such as trifluralin, terbaacil, solan, and paraquat. Post-harvest, hydrodistillation was employed to extract the oils which were then subjected to gas chromatography and mass spectrometry. One of the hybrids showed a high level of geraniol; this hybrid was grown for a short time in southern Alberta, Canada for geraniol production but for an unknown reason, the plants did not survive the second year.

Rust, otherwise known as *Puccinia menthe*, was reported as the major disease of the sterile *Monarda* (Mazza, 1993) causing defoliation, stem damage and degeneration of plants. Recommendations for control of rust include application of the herbicide paraquat in early spring. This article also reported variations of essential oil yields between about 0.65 and 1.2 g/100 g of fresh plant material or between about 60-125 kg of oil/ha.

As described earlier, Carvacrol and Thymol have both antiseptic and antimicrobial activities and have been used accordingly. It also appears that one or both may be used as an herbicide of sorts, specifically, a biochemical fungicide for control of moss and liverwort. Geraniol is used most often for its scent in products such as perfumes. Thymoquinone, as mentioned earlier, is indicated as having therapeutic effect in the treatment of some mammalian cancers and other ailments.

In the present invention, it was postulated by the inventors that levels of oil, and perhaps quality of the oil, in the *Monarda fistulosa* plants may be at least somewhat dependent on planting and growth methods. Finding a dependable means of growing and harvesting oil from *Monarda fistulosa* in a manner selective for the desired oil would be beneficial. Developing a method that minimized use of herbicides and pesticides was also desirable in order to produce high quality oil unadulterated by chemical use.

For the most part, historically *Monarda fistulosa* has been cultivated as a seed for wildflower planting purposes rather than for oil production albeit some plants have been selected for geraniol production

*Monarda fistulosa* is an erect aromatic annual or perennial plant which bears pretty pinkish/lavender flowers. It is often used in wildflower seed mixes and in prairie restoration projects. Previously recommended methods for cultivation of *Monarda fistulosa* include planting rates of between about 0.25 lbs/acre and 2 lbs/acre, and cutting and or splitting the plants to increase them, timing of harvest, etc. In terms of labor and time costs, the previous methods are not ideal. Further, none of the literature purports to claim these methods increase the average levels of certain components in the oil such as thymol, carvacrol or thymoquinone.

What was needed was a method of producing *Monarda fistulosa* on a commercial scale and economically to produce an oil comprising relatively high levels of carvacrol, and/or thymoquinone and/or thymohydroquinone. A desirable method of doing so would reduce cultivation expenses and labor while providing a dependable means for a reliable harvest of the multi-use oil and its constituents.

It was therefore one objective of the present invention to determine appropriate seed planting rates and spacing to provide and encourage efficient production of plants bearing oil having higher levels of carvacrol and/or thymoquinone and/or thymohydroquinone.

It was another objective of the present invention to provide a method of growing *Monarda fistulosa* that would result in least expense for weed and/or rust control while providing high levels of desired essential oil or oils.

It was another objective of the present invention to provide a method for cultivating *Monarda fistulosa* that reduced the amount of fuel required, specifically by reducing the need for fuel used to apply herbicides, and boiler fuel used in distilling/cooking through unwanted weeds mixed in with the *Monarda*.

It was another objective of the present invention to provide a method for planting, cultivating and harvesting *Monarda fistulosa* that provided an economically viable manner of producing one or more essential oils.

It was a primary objective of the present invention to provide a method of cultivation of *Monarda fistulosa* that increased consistent results of high quality and relatively high production levels of the desired oil constituents.

SUMMARY OF THE INVENTION

The present invention includes a recommended planting rate and cultivation methodology that has heretofore been unknown. The method increases germination, decreases herbicide use and fuel use, increases the yield of *Monarda fistulosa* oil, and increases the yield of certain essential oils such as carvacrol, thymoquinone, and thymohydroquinone, alone or in various combinations of increasing yields of these oils.

Although known recommended planting rates for *Monarda fistulosa* ranged from about 0.25 to up to 2 lbs per acre (*Monarda fistulosa* contains 1,120,000 seeds/lb) for producing seeds for use in wildflower seed mixes and prairie grasses, it was surprisingly found that these rates did not provide the better means for cultivating and harvesting the plants and the desired essential oils they contained. At the rates previously recommended, weed pressure causes a decrease in yield of oil, and causes an increase in levels of unwanted contaminants associated with those weeds (e.g. aromatic sap from the weeds) which may appear in the harvested oil, decreasing its quality. These contaminants may reduce oil quality by up to 40%. Removing these weeds from a field of *Monarda fistulosa* to avoid the contamination and downward pressure on yield requires more fuel to be used in the operation to remove/destroy those weeds and/or requires herbicides which, in turn, may negatively impact oil yield and quality. The result is a reduction in the efficiency of the overall operation.

The inventors experimented in a 12-acre field, drill seeded at differing rates. Specifically, 2.0, 2.5, 3.0, 3.5, 4.0, 4.5 and 5.0 pounds of seed per acre. Photos taken 5 days prior to harvest showed a dramatic decrease in weeds at the higher rates versus those in the lower planting rates at the first harvest. Photos taken 30 days after harvest showed that the lower planting rates of *Monarda fistulosa* planting resulted in higher weed pressure even at this stage which, in turn, will translate to increased pressure the following season.

Further, it was determined that rolling the ground after either drilling or broadcast seeding increases germination, or use of a cultipacker to pack the soil even tighter may provide even higher levels of germination. Theoretically, the soil compression provided by the roller or cultipacker provides a better barrier for retaining moisture and for protection against birds or other pests while the seeds germinate.

In contrast to prior methods, the present invention recommends planting rates ranging from about 2.5 lbs/acre to about 5 lbs/acre or, more preferably, around about 4 lbs/acre either via broadcast seeding or drilling. This is about twice the planting rate that has previously been recommended for growing *Monarda fistulosa*. Further, the method includes rolling the ground securing the soil around drilled or broadcast seeds to seal in moisture and protect the seeds. Alternatively, *Monarda* may be plug planted, but the population density must be at least comparable to that expected to result from the planting rates herein recommended. Specifically, plug planting at a rate between about 45,000 and about 60,000 plugs per acre is recommended.

In some embodiments, the method advises no harvest the first season but, rather, regular mowing. Some embodiments provide recommended methods of weed control that are plant-population dependent, others employ herbicides or some combination of the two. Recommendations regarding pesticide use and fertilizer application are also provided.

The new method advocates certain practices related to harvesting *Monarda fistulosa* for best yield of the desired oil and increase in certain constituents of that oil. The method also describes means and methods for separating the oil from the plant. Finally; the method includes recommended best practices for the maintenance of the perennial and number of seasons for production prior to destruction.

In short, one of the preferred embodiments includes drilling seed or broadcast seed application of between about 2.5 lbs and about 5 lbs per acre, more preferably between about 3.5 lbs and about 4.5 lbs per acre, and most preferably around 4 lbs per acre. Once seeded, means to seal moisture in and around the seed are employed. A recommended method is the use of a roller across the field to both compact the soil to a degree and to seal in moisture. Alternatively, or in addition, a cultipacker may be employed. Seeding is done in the spring of the year.

Alternatively, seedlings may be nursery grown and transplanted as plugs. It is important that regardless of whether seeding or plug planting, the plant density is about the same. Recommended rates for plug planting are between about 45,000 and about 60,000 per acre. *Monarda fistulosa* and other *Monarda* types may all benefit from this cultivation method. Further, the maturity of the plant may influence its essential oil profile. Specifically, this invention may be used to grow, harvest and obtain oil from at least those listed in Table 1.

TABLE 1

*Monarda Didyma* L.
*Monarda Media* Willd
*Monard Menthifolia* Graham

*Monarda bradburiana* Beck
    *Monarda fistulosa* Sims, nom. inq.
    *Monarda rigida* Raf.
    *Monarda villosa* M. Martens
*Monarda media* Willd.
*Monarda* × *medioides* Duncan [*fistulosa* × *media*]
*Monarda dressleri* Scora [excluded]
*Monarda fistulosa* L.
*Monarda fistulosa* L. ssp. *Fistulosa*
*Monarda fistulosa* L. ssp. *fistulosa* var. *fistulosa*
*Monarda fistulosa* L. ssp. *fistulosa* var. *menthifolia* (Graham) Fernald
*Monarda fistulosa* L. ssp. *fistulosa* var. *mollis* (L.) Benth.
*Monarda mollis* L.
*Monarda scabra* Beck
*Monarda fistulosa* L. ssp. *fistulosa* var. *rubra* A. Gray
*Monarda fistulosa* L. var. *brevis* Fosberg & Artz
*Monarda fistulosa* L. ssp. *brevis* (Fosberg & Artz) Scora, ined.

Other objects, features, and advantages of the present invention will be readily appreciated from the following description. The description makes reference to the accompanying drawings, which are provided for illustration of the preferred embodiment.

However, such embodiment does not represent the full scope of the invention. The subject matter which the inventor does regard as his invention is particularly pointed out and distinctly claimed in the claims at the conclusion of this specification. The invention has been disclosed in such a way as to enable one of ordinary skill in the art to practice the invention.

BRIEF DESCRIPTION OF THE DRAWINGS

FIG. 5 chart showing levels of constituents in the oil harvested from plants grown according to the described cultivation process.

DETAILED DESCRIPTION OF THE INVENTION

The present invention comprises planting seed of *Monarda fistulosa* or any of the species listed in Table 1 in a field at a rate between about 2.5 lbs per acre and about 5 lbs per acre and more preferably between about 3.5 and 4.5 lbs per acre. Alternatively, plants 14 may be plug planted at a rate between about 45,000 and about 60,000 per acre. The field 12 should be mowed regularly the first year without harvesting the plant or its heads/blooms, and then harvesting it in years thereafter. Harvest may include stems (generally the section above the ground level), along with leaves and heads, or may be more limited to harvesting just heads without stems and leaves. The lifetime of plants 14 for a single planting is typically 5-7 harvests, but may be longer or shorter depending on soil conditions, climate and husbandry practices. The equipment used to condition the field, plant the seed (where seeding is employed rather than plug planting), or, alternatively, plant the plugs, mow the plants, cut the plants, and gather the heads and leaves or whole plants may each be of any type readily known and understood by one of skill in the art. Examples of each of these types of equipment are provided herein by machine producer's brand name but they are provided strictly for purposes of example, and not for limitation.

Figure 1:
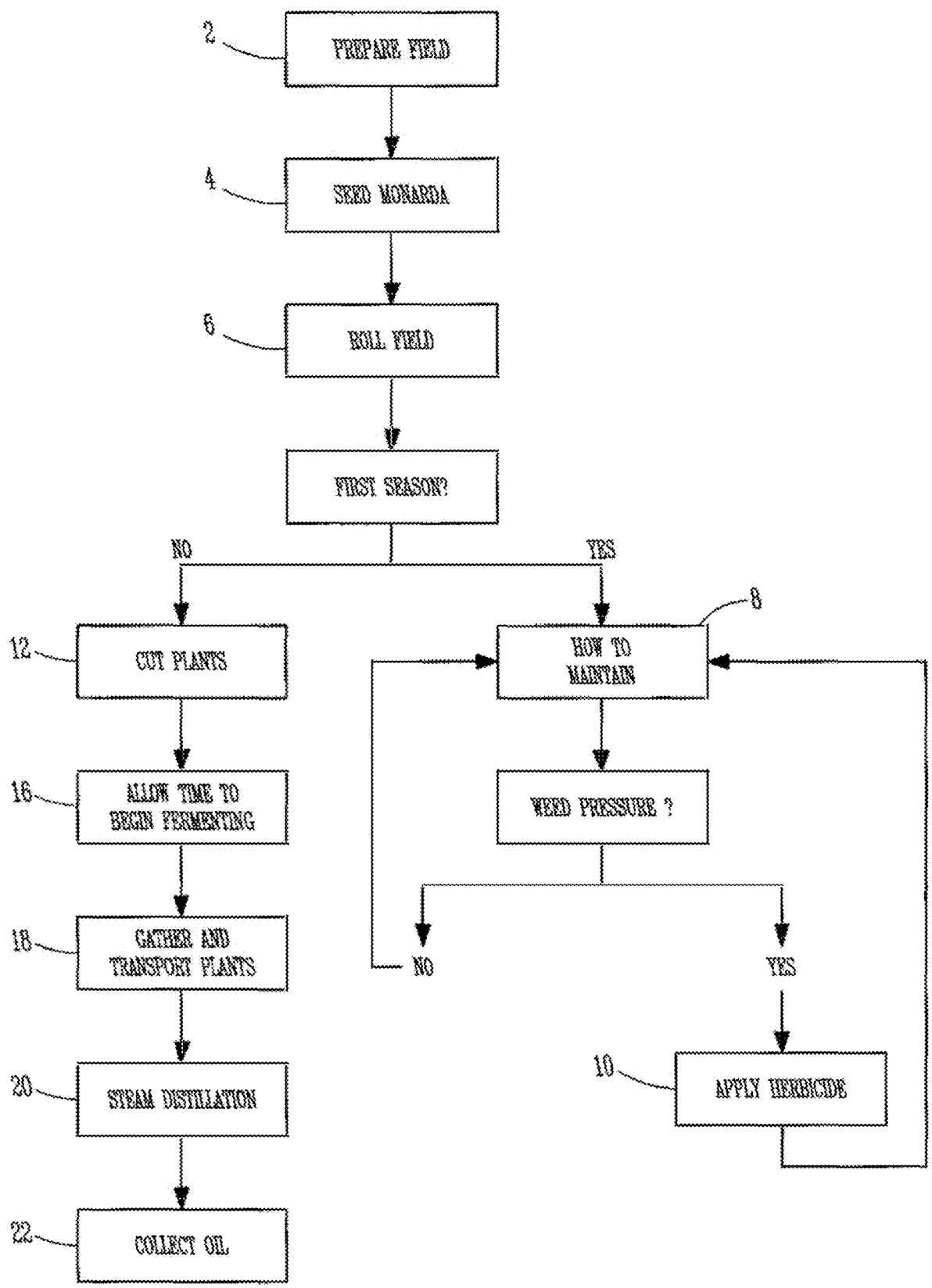
FIG. 1 flow chart describing the cultivation process.
Figure 2:
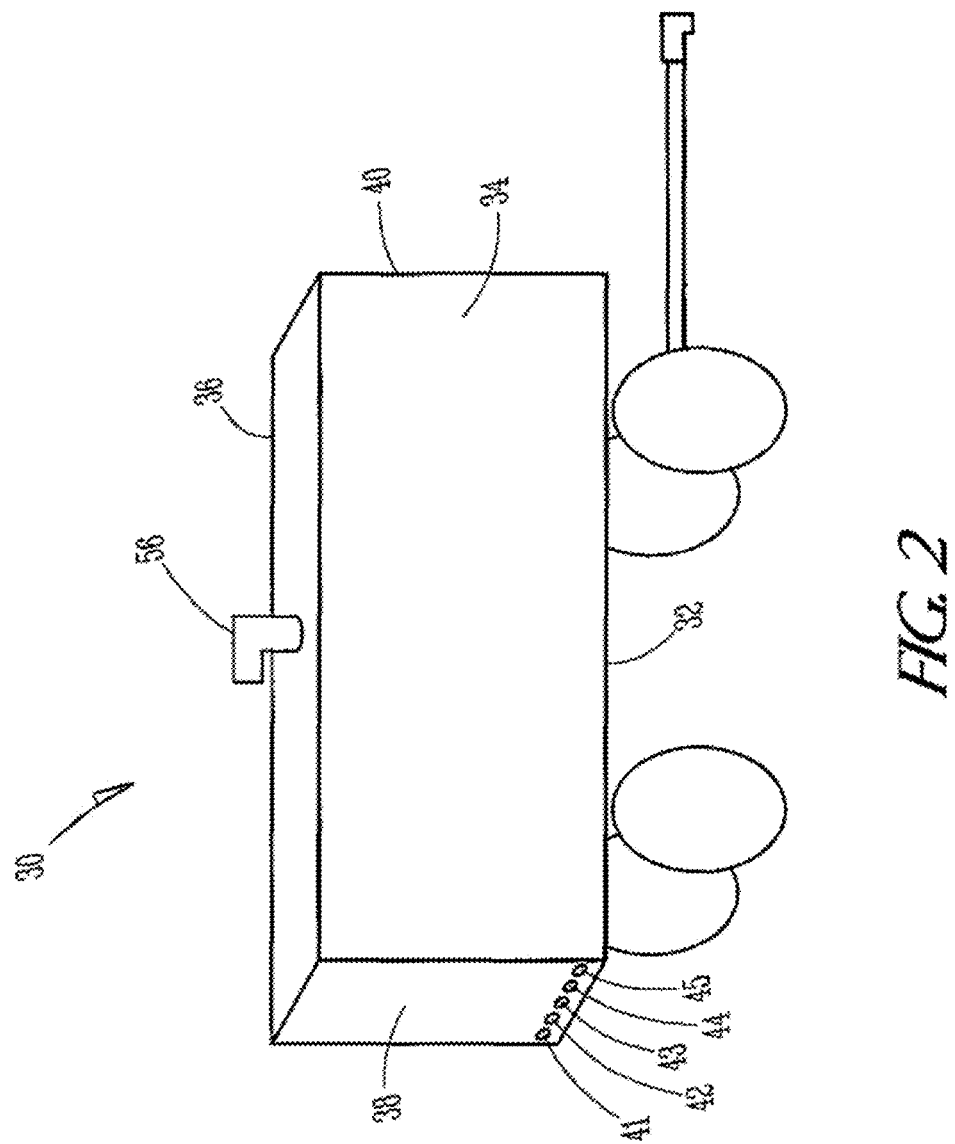
FIG. 2 perspective view of means for transporting.
Figure 3:
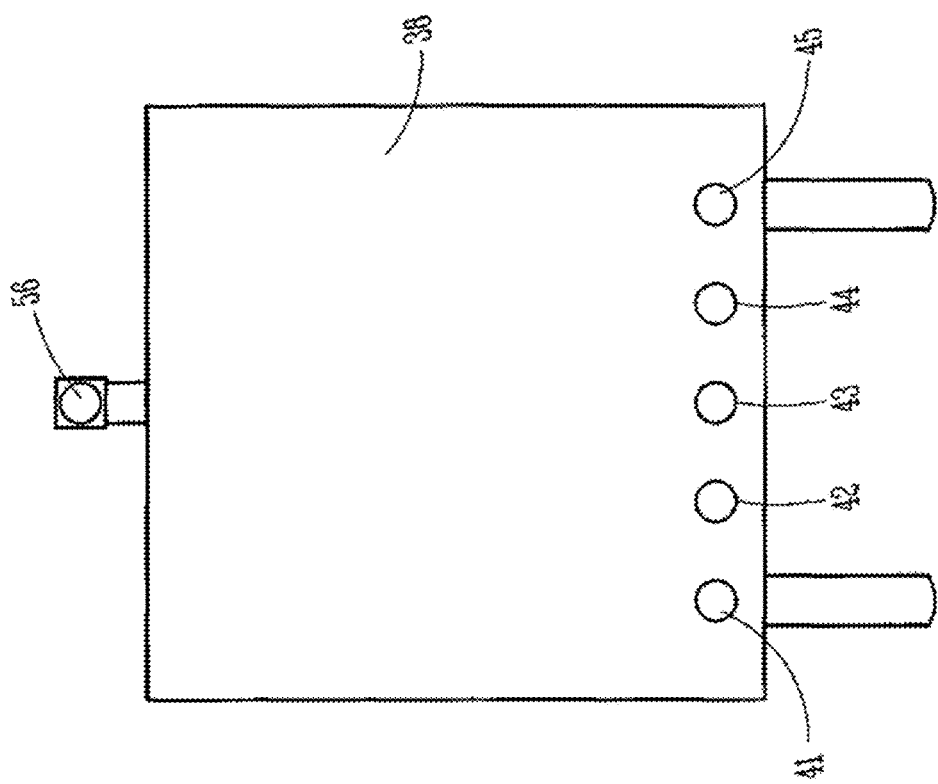
FIG. 3 end view of means for transporting.
Figure 4:
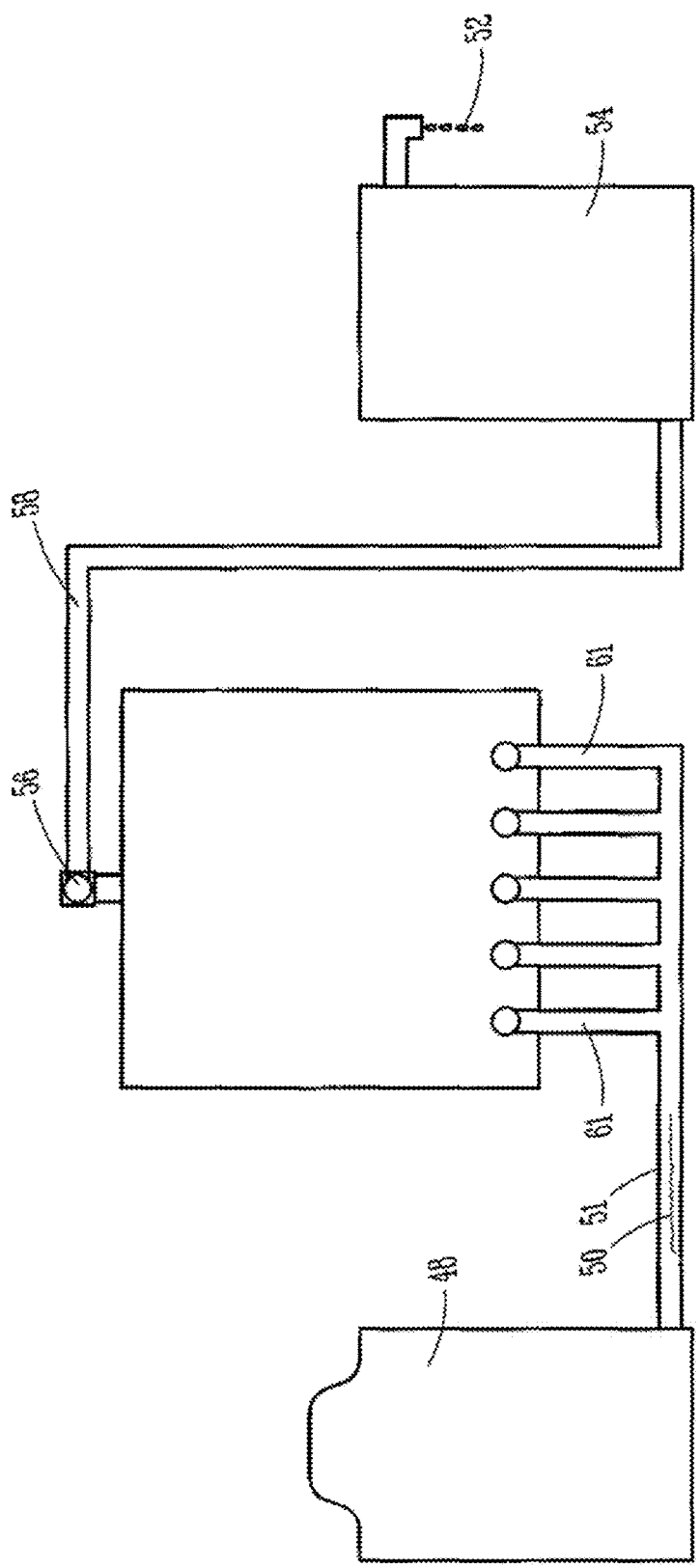
FIG. 4 schematic illustrating steam distillation components.

Referring now to FIG. 1 the field 12 is prepared 2 by routine tilling, field cultivating, discing or other means for turning or loosening the upper layer of soil. For example and not for limitation, a disc 16 by CaseiH, Krause, or other implement dealer may be used. Depending on soil type, fertilizer may or may not be applied. Next, the field is seeded 4. Seed 10 may be drilled or broadcast. When drilled, spacing of about 8 inches to about 10 inches is desired. Although many permissible drills exist, two examples are produced by Brillion or Taka. Alternatively, the seed 10 may be broadcast. Again, a variety of acceptable broadcasting devices are available such as a TerraGator. In either case, broadcasting or drilling, seed 10 should be planted at the rates mentioned above.

Alternatively, plants may be plug planted at generally even spacing for about 45,000 to about 60,000 plugs per acre. The plugs may be planted in rows or groups or generally equidistant.

In a preferred method, planting (via drill or broadcast or other means) is preferably followed by rolling or other soil compression activities 6. An example of an acceptable roller device is a Riteway model 4300 which weighs between 15,800 lbs and 23,500 lbs. Rolling or other compression actions are preferably completed the same day as the field is cultivated and also, and more critically, within 2 to 48 hours after drilling or broadcasting seed. The timing is recommended in order to avoid overdrying the soil, protect the seeds from birds, and to compress the soil enough to create a seal to assist in retaining the remaining moisture to improve germination percentages for the seeds.

In another method, the soil may be prepared to minimize clods and provide soil texture amenable to plug planting. Thereafter, plugs may be planted, and then lightly rolled to seal the ground, or if row planted, soil may be tamped between rows. However, a sealing process is not critical for the transplanted plants.

During the first season (whether seeded or plug planted), the field 12 should be mowed 8 on a regular basis. Depending on rainfall, soil and climate conditions, mowing may be done as often as 4-6 times in a season or as infrequently as 2-4 times. Mowing frequency is dictated by the height of the plants. Weeds grow much faster in the first season than does the *Monarda*, so mowing is aimed to keep the weed height reduced to allow the *Monarda* to become established. Mowing should be done to maintain the field between about 8 and 10 inches tall and, more preferably when they are about 8 inches tall, as many times in the first season as needed to keep the plants less than about 8 to 10 inches high. At the end of the first growing season, the plants are preferably left around 8 inches tall to catch snowfall. Any suitable mowing machine 24 may be employed. For example, several models of the Woods bat-wing mower work well.

It is foreseeable that seeds 10 planted in a bare field 12 the first season where ground cover or crop previously existed may be subjected to some weed pressure early in the growing season of that first year. When this occurs, application of Assure II or Select Max work well. Other herbicides applications 10 are also likely to be effective, however, broadleaf herbicides should not be used because they damage *Monarda*.

The second growing season is unlikely to require any herbicides, however, Assure II, Basagran and SelectMax are but a few examples of herbicides that may be employed if needed. Due to the planting rate, the compression of the soil, and multiple mowings in the first season, plants will emerge early and tend to grow quickly. *Monarda fistulosa* plants 14 produce their own herbicidal chemicals one of which is carvacrol. These chemicals act to control any weeds that are not simply physically crowded out by the *Monarda*. The action of the carvacrol effects germination of the weed seeds. The planting rate, the growth rate, the size of the plants, and the *Monarda*'s own chemical defenses result in a crop that typically requires no further herbicide treatments but for, perhaps, an occasional weed patch which may be controlled via hand sprayer or physical removal.

In midsummer, *Monarda fistulosa* plants produce a lavender colored fragrant flower. The plants are harvested at flower peak which, in the Midwest United States, is generally early to mid-July. The flowers contain the essential oil as do the stems and the leaves.

Harvest of *Monarda fistulosa* fields cultivated in the manner of the present invention may be accomplished in several ways using various equipment. A preferred method is to employ a MacDon draper or any other cutting machine to cut 12 the plants 14 with flowers attached and leave them lay where they were cut. The cut plants may remain in the field for up to about 12-to about 24 hours but oil can also be reasonably harvested if the plants are left as little as 2-6 hours or 4-6 hours 16. It is best, but not critical, that these hours be warm and sunny. Leaving the plants lay starts the process of oil release from the inter-cellular pockets within the plant. The cut plants 14 are then gathered by a suitable device such as a forage chopper 18 and placed in means to transport 30 them from the field.

Alternatively, the plants (alternatively, the flower heads only, or the flowers and leaves only) may be harvested freshcut and transported directly to the still. It is theorized that senescence of the flower heads caused by the harvest process results in release of oil and may also influence the constituents of the distilled oil. Specifically, flower senescense is the terminal phase of developmental processes that lead to the flower's death. Those processes include wilting, shedding of flower parts, and fading. The flowers' senescence is much faster than that of other plant parts and certain stimuli may upregulate certain catabolic processes. Those processes may cause the breakdown and remobilization of different cellular constituents. Further, the resources in the flower may be transported within the plant to meet other needs in an ultimate recycling and conservation of resources system. It is theorized that the constituents of the harvested oil differ relative to post-harvest time lapse and, therefore, distillation of flower heads at a freshcut stage may result in oil having different profiles.

In one embodiment, means to transport 30 the cut plants 14 comprises a generally watertight wagon having a floor 32, two sides 34, 36, and two ends 38 and 40 with multiple ports 41-45 near the floor 32 in one of the ends 38 or 40. The wagon 30 just described is used in one of several methods for removing oil from *Monarda fistulosa*, specifically steam distillation.

Steam distillation of oil from plants is old in the art and works on the principle that steaming the cut plants encourages release of the plants' essential oils via rupture of the plant's oil sacs which are taken up with the steam. During steam distillation 20 a boiler 48 creates steam 50. The steam 50 travels through a conduit 51 to said means to transport 30 (or some other container wherein said plant parts are present) and enters through ports 41-45 near the floor 32. The steam travels upward moving oil 52 that has been released upward with the steam 50. The steam 30, with oil 52, is removed through the port 56 into a second conduit 58. The steam 50 and oil 52 is run through a condenser 54 which causes the oil 52 and water in the steam 50 to condense and allows the oil 52 to be separated and recovered 22. When using the wagon 30, a steam input 61 is connected to each port 41-45. Steam is injected into the wagon and, as it travels upwards, oil 52 from the plants 14 is removed with the steam. The steam and oil then exit the top of the wagon through the port 56 and flow into or through one of many different kinds of condensers 60 where the oil 52 is recovered and the condensed steam (water) may or may not be reheated and reused in the process.

During distillation, the essential oils are separated from the distillate in an order characteristic of the oil and related to the boiling point of that oil. (See Table 1 below) Thymoquinone separates just before thymol and carvacrol and thymohydroquinone separates just after carvacrol.

TABLE 2

| compounds | molecular weight | boiling points |
| --- | --- | --- |
| alpha pinene | 136.24 | 155 |
| alpha thujene | 136 | 155 |
| alpha terpinene | 136.237 | 164 |
| beta myrcene | 136.23404 | 167 |

TABLE 2-continued

| compounds | molecular weight | boiling points |
|---|---|---|
| para cymene | 134.22158 | 179 |
| gamma terpinene | 136.23404 | 182 |
| linalool | 154.252 | 198 |
| terpinene-4-ol | 154.249 | 212 |
| thymoquinone | 164.204 | 231 |
| thymol | 149.66 | 232 |
| carvacrol | 150.221 | 238 |
| caryophyllene | 204.356 | 256 |
| thymohydroquinone | 166.217 | 306 |

The method of cultivation just described increases germination, decreases herbicide use and fuel use, and increases the yield of *Monarda fistulosa* oil generally, and specifically, effects relative amounts of carvacrol, thymol, and thymoquinone (TQ) and thymohydroquinone (THQ). Oil yield from various methods of cultivation are presented on Table 1. At least after the first year's growth, and more commonly also after the first year including harvest, the TQ and THQ levels, together, may constitute about 25% to 35% and up to about 50% of the oil distilled and either carvacrol or thymol constitute over 20% of the oil distilled, or together constitute over 20% of the oil distilled.

The above-mentioned cultivation method results in oil content that is commercially desirable, namely, containing increased amounts of carvacrol, thymol, thymoquinone, and thymohydroquinone. Although known recommended planting rates for *Monarda fistulosa* ranged from about 0.25 to up to 2 lbs per acre (*Monarda fistulosa* contains 1,120,000 seeds/lb), it was surprisingly found that these rates did not provide the better means for cultivating and harvesting the plants and obtaining the desired essential oils they contained at the level of oil quality and profile desired. Oil quality of the present invention is high at least partially due to the reduction and near elimination of weed pressure and its resulting contamination. The quality may also be partially attributed to low uses of herbicides or pesticides. The oil constituent profile is also beneficially effected by control of weed pressure under less chemical pressure and the cultivation practices described herein. It is believed also that harvesting methodology at least relative to time between harvest and distillation, and perhaps also relative to plant parts, also attributes to oil profile.

Thus, the present invention has been described in an illustrative manner. It is to be understood that the terminology that has been used is intended to be in the nature of words of description rather than of limitation.

Many modifications and variations of the present invention are possible in light of the above teachings. For example, distillation may be accomplished in other ways; seeds may be planted via hand, or via traditional planters, or other seed planting devices not yet known. New effective herbicides may become known. New *Monarda* hybrids may be developed and it may be determined that other mans may be employed to increase oil production even more, specifically the level of carvacrol or of thymoquinone or thymohydroquinone in the *Monarda*. Therefore, within the scope of the appended claims, the present invention may be practiced otherwise than as specifically described.

What is claimed is:

1. A method of producing oil comprising thymoquinone and/or thymohydroquinone, the method comprising planting at least one species of *Monarda* plants producing oil by broadcast seeding at a rate of greater than 3.0 pounds per acre to about 5 pounds per acre in a field, growing and harvesting said plants and allowing said plants to lay in the field for a plurality of hours.

2. The method of claim 1 wherein said plurality of hours comprises a range between about 12 hours and about 24 hours.

3. The method of claim 1 wherein said plurality of hours comprises a range between about 2 hours and about 6 hours.

4. The method of claim 1 further comprising separating said oil using a process comprising distillation.

5. A method of producing oil comprising thymoquinone and/or thymohydroquinone, the method comprising planting at least one species of *Monarda* plants producing oil by planting about 45,000 to about 60,000 plugs per acre in a field, growing and harvesting said plants and allowing said plants to lay in the field for a plurality of hours.

6. The method of claim 5 wherein said plurality of hours comprises a range between about 12 hours and about 24 hours.

7. The method of claim 5 wherein said plurality of hours comprises a range between about 2 hours and about 6 hours.

8. The method of claim 5 further comprising separating said oil using a process comprising distillation.

9. A method of producing oil comprising thymoquinone and/or thymohydroquinone, the method comprising planting at least one species of *Monarda* plants producing oil by broadcast seeding at a rate of greater than 3.0 pounds per acre to about 5 pounds per acre, growing and harvesting said plants and allowing said plants to senesce for a plurality of hours.

* * * * *